: US008236914B2

(12) United States Patent
Potisek et al.

(10) Patent No.: US 8,236,914 B2
(45) Date of Patent: Aug. 7, 2012

(54) SELF-ASSESSING MECHANOCHROMIC MATERIALS

(75) Inventors: Stephanie L. Potisek, Urbana, IL (US);
Douglas A. Davis, Champaign, IL (US);
Scott R. White, Champaign, IL (US);
Nancy R. Sottos, Champaign, IL (US);
Jeffrey S. Moore, Savoy, IL (US)

(73) Assignee: Board of Trust of the University of Illinois, Urbana, IL (US)

( * ) Notice: Subject to any disclaimer, the term of this patent is extended or adjusted under 35 U.S.C. 154(b) by 0 days.

(21) Appl. No.: 12/693,801

(22) Filed: Jan. 26, 2010

(65) Prior Publication Data
US 2010/0206088 A1    Aug. 19, 2010

Related U.S. Application Data

(63) Continuation of application No. PCT/US2008/071083, filed on Jul. 24, 2008.

(60) Provisional application No. 60/952,550, filed on Jul. 27, 2007.

(51) Int. Cl.
*C08F 120/18* (2006.01)
*G01B 11/16* (2006.01)
*C08G 63/00* (2006.01)
*C08G 63/66* (2006.01)
*C08G 65/00* (2006.01)

(52) U.S. Cl. ....... 526/329.7; 73/762; 528/363; 528/361; 528/392

(58) Field of Classification Search ............. 73/762; 528/363, 361, 392; 526/329.7
See application file for complete search history.

(56) References Cited

U.S. PATENT DOCUMENTS

| | | | |
|---|---|---|---|
| 4,721,769 A | 1/1988 | Rubner | |
| 4,916,211 A * | 4/1990 | Rubner | ............ 528/480 |
| 6,518,330 B2 | 2/2003 | White et al. | |
| 6,858,659 B2 | 2/2005 | White et al. | |
| 7,566,747 B2 | 7/2009 | Moore et al. | |
| 7,569,625 B2 | 8/2009 | Keller et al. | |
| 7,612,152 B2 | 11/2009 | Braun et al. | |
| 7,723,405 B2 | 5/2010 | Braun et al. | |
| 2006/0111469 A1 | 5/2006 | White et al. | |
| 2008/0299391 A1 | 12/2008 | White et al. | |
| 2008/0305343 A1 | 12/2008 | Toohey et al. | |

OTHER PUBLICATIONS

Todres "Recent advances in the study of mechanochromic transitions of organic compounds", J. of Chemical Research, Feb. 2004, 89-93.*
Kim et al. "A mechanochromic smart material", Polymer Bulletin, 31, 1993, 367-374.*
International Searching Authority, "International Search Report and Written Opinion for PCT/US2008/071083", Dec. 3, 2008, Publisher: European Patent Office, Published in: EP.
Galiotis, et al., "The Solid-State Polymerization and Physical Properties of Bis(ethyl Urethane) of 2,4-hexadiyne-1,6-diol", "Journal of Polymer Science: Polymer Physics", 1983, pp. 2483-2494, vol. 21.
Nallicheri, et al., "Investigations of the Mechanochromic Behavior of Poly(urethane-diacetylene) Segmented Copolymers", "Macromolecules", 1991, pp. 517-525, vol. 24, No. 2.

* cited by examiner

*Primary Examiner* — Michael M Bernshteyn
(74) *Attorney, Agent, or Firm* — Blanchard & Associates

(57) ABSTRACT

A mechanochromic material includes a polymer having a backbone containing a mechanophore.

11 Claims, 10 Drawing Sheets

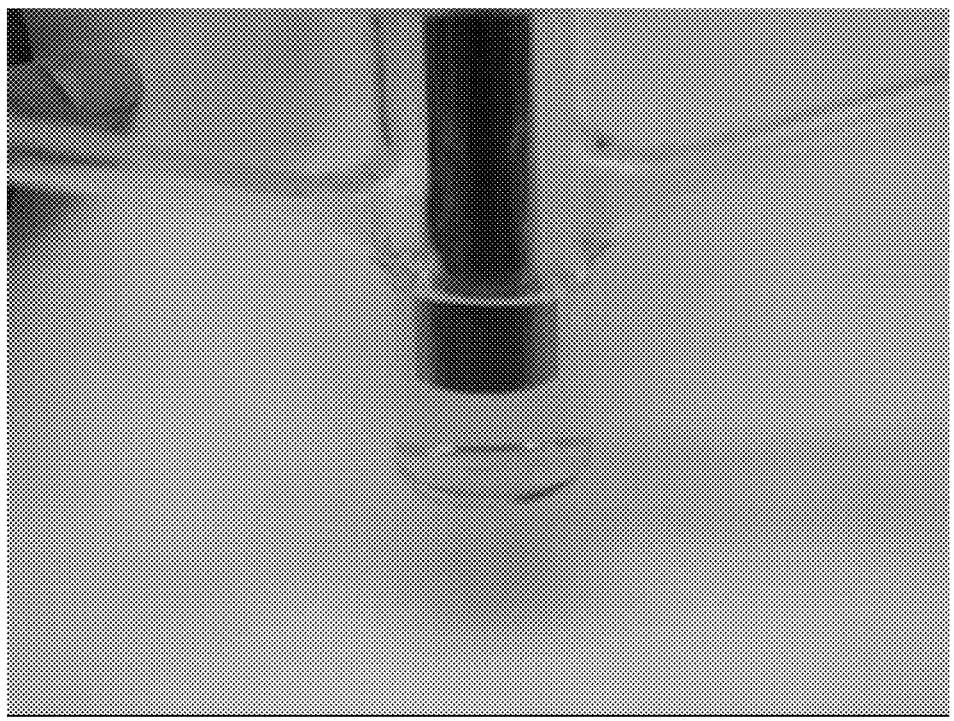
FIG. 8 a (before)
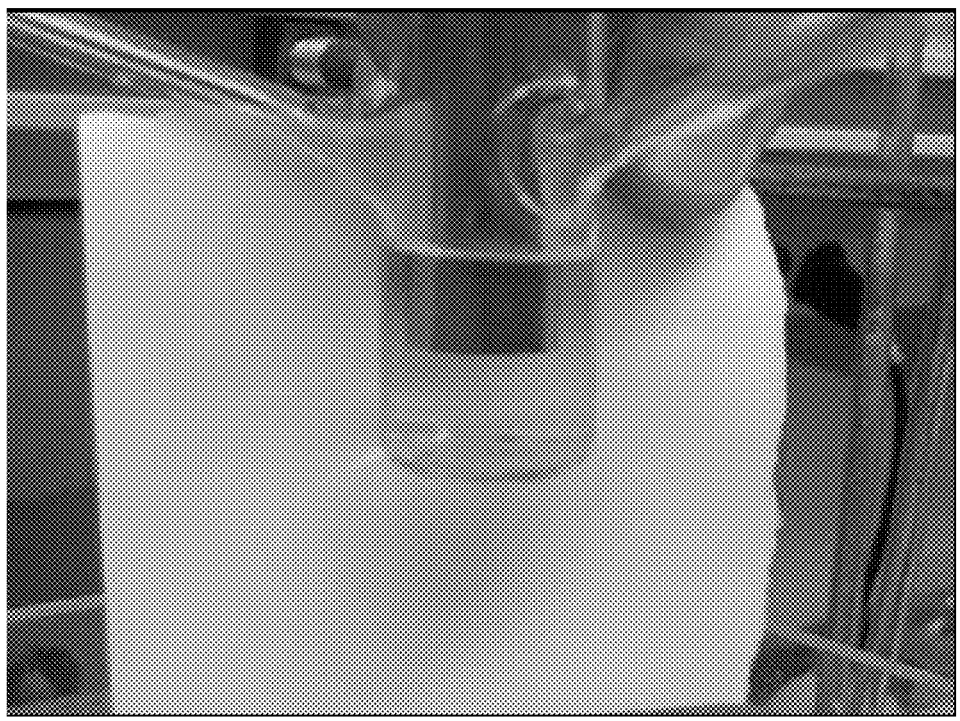
FIG. 8 b (after)

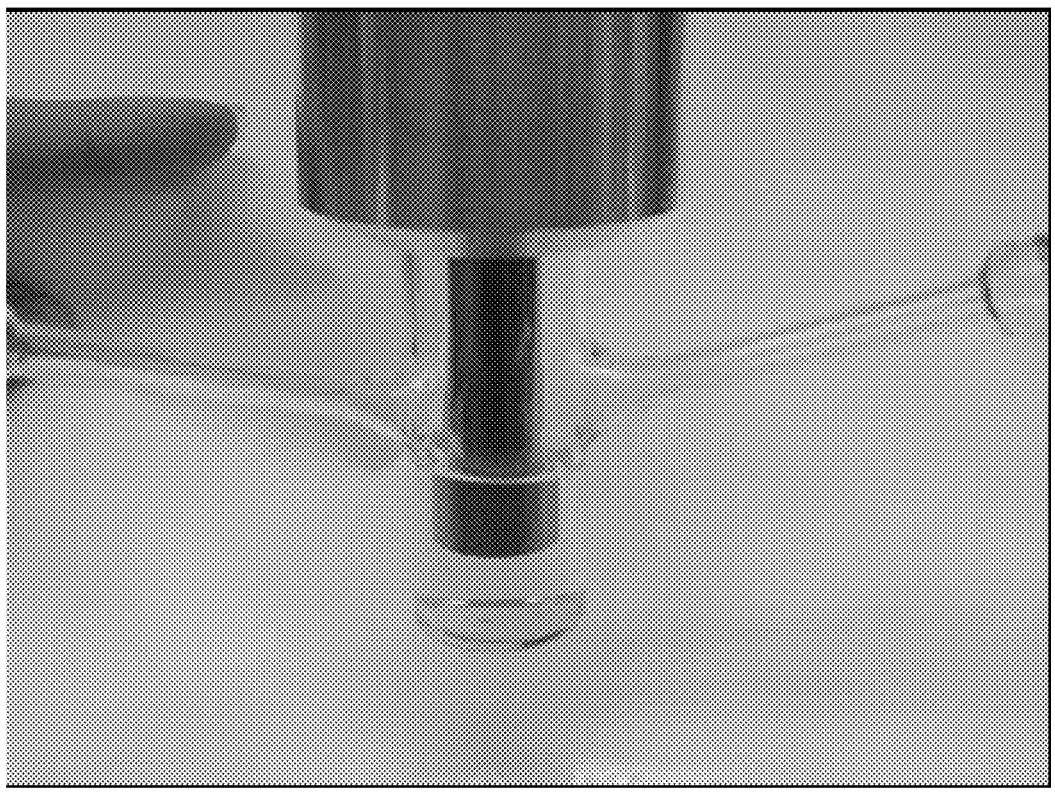
FIG. 8 c (2 hours under ambient light)

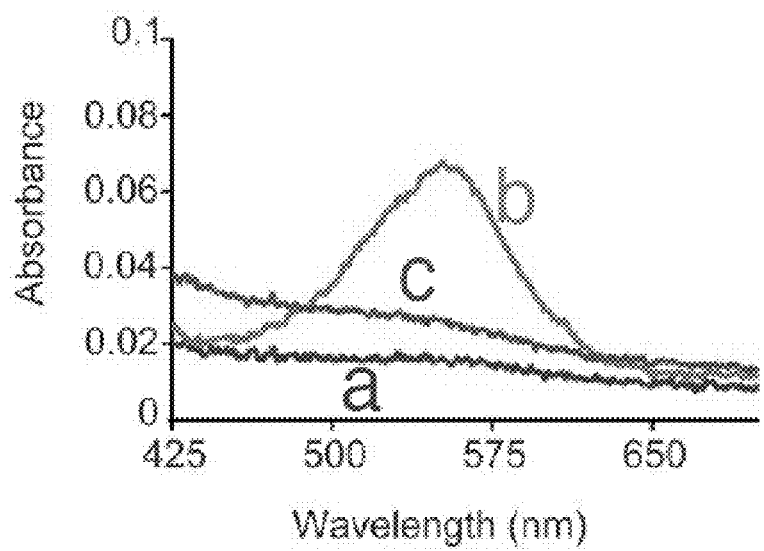
FIG. 9
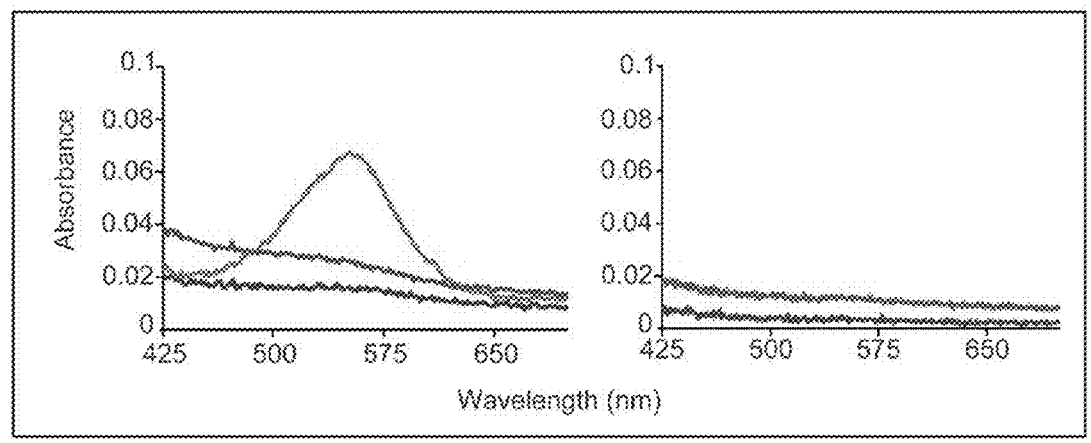
Figure 11    Midpoint    Terminus

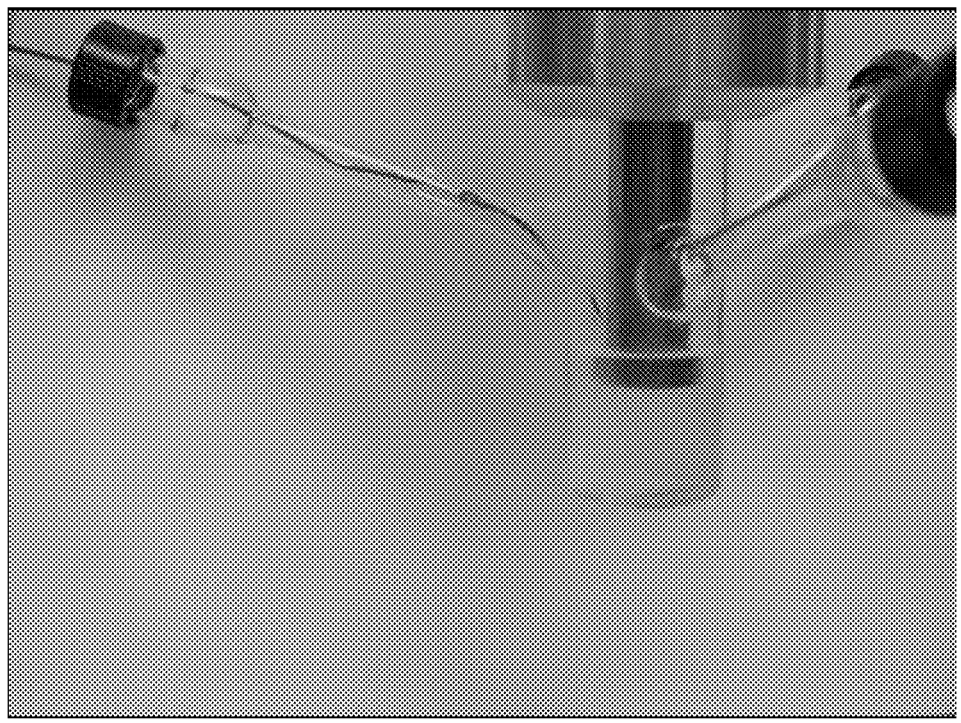
FIG. 10 a (before)
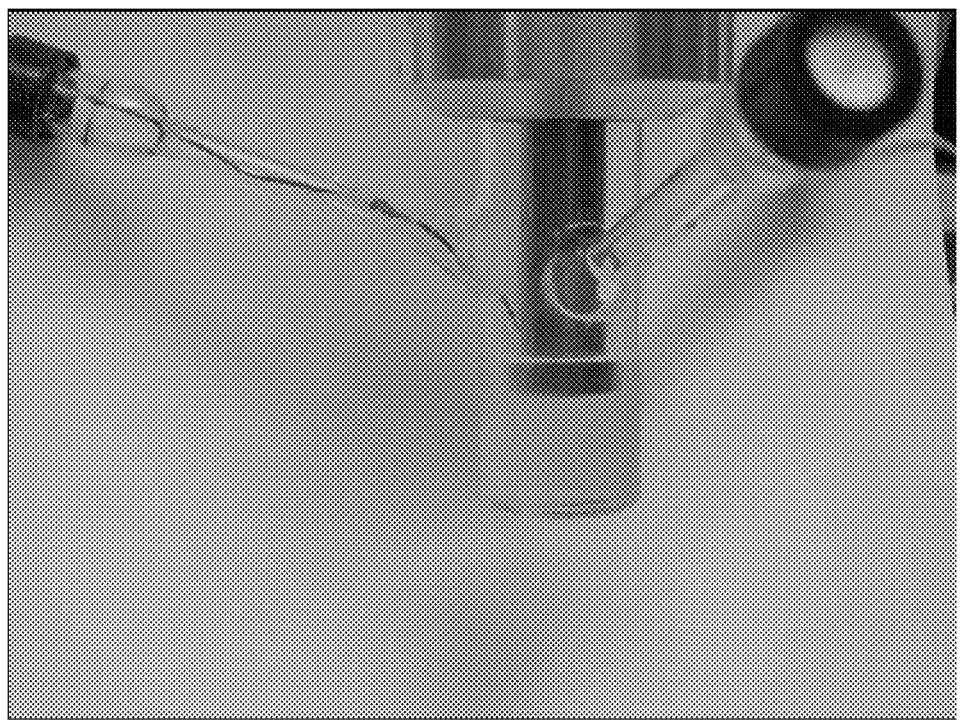
FIG. 10 b (after)

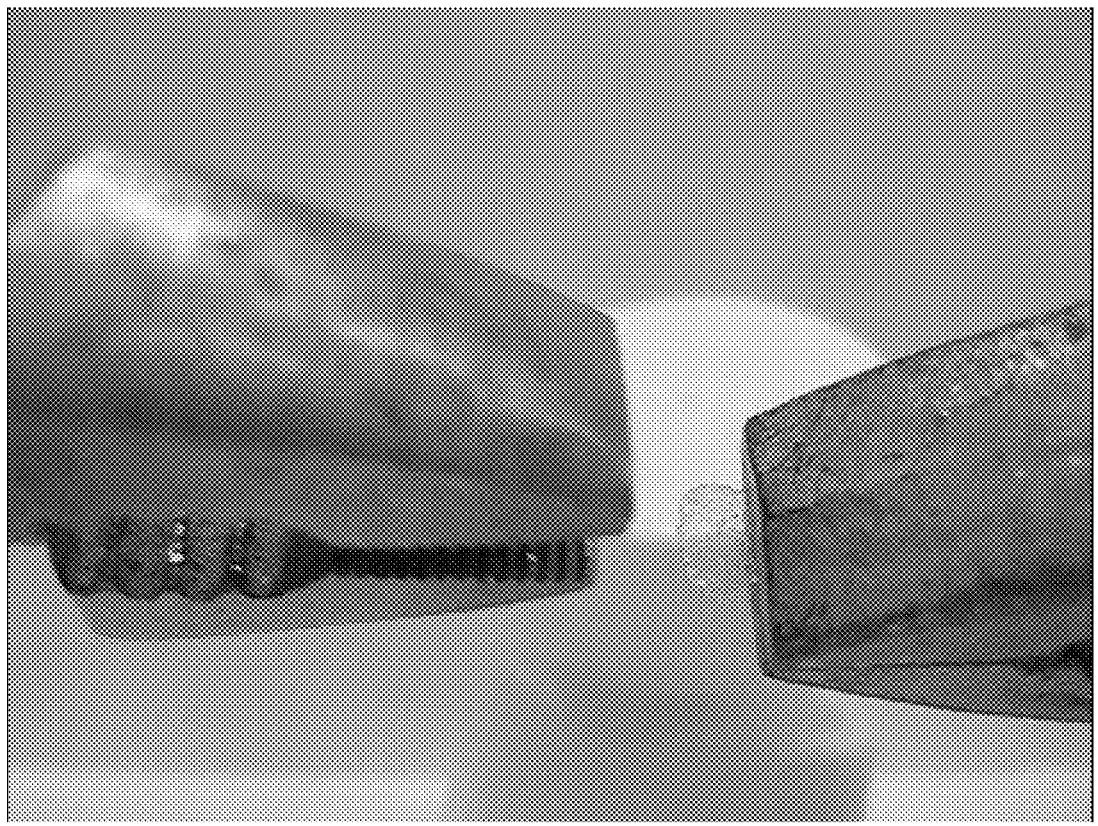
Figure 12 (170 kDa, 0.4 wt% spiropyran)

SELF-ASSESSING MECHANOCHROMIC MATERIALS

REFERENCE TO RELATED APPLICATIONS

This application is a continuation of PCT/US2008/071083 entitled "Self-Assessing Mechanochromic Materials" filed Jul. 24, 2008, which was published in English and claimed the benefit of U.S. Provisional Application No. 60/952,550 entitled "Self-Assessing Mechanochromic Materials" filed Jul. 27, 2007, which are incorporated by reference in their entirety.

BACKGROUND

Polymer materials are ubiquitous in everyday life and are used in various applications (medical, automobile, electronics, structural etc.). These materials experience stress through normal use, which can lead to damage and failure of the product. Having the ability to detect damage and locate areas under high stress in situ is essential to eliminating failure of the material.

Several examples of self-assessing materials are known in the patent literature. The simplest incorporate a colored substance into the matrix in the form of capsules[1] or hollow fibers.[2] Initially the color is not visible, but, upon damage to the matrix, the capsules or fibers rupture and expose the colored fluid or solid. In some cases, a two part system is utilized wherein a colorless compound mixes with an activator upon the rupture of their respective containers causing a color change. The disadvantage of these systems is that the fibers and capsules need to be evenly dispersed throughout the matrix, so that the damage inducing force has a large chance of intersecting the particles.

Another approach is the use of triboluminescent materials, which give off flashes of light in response to stress or damage.[3] These materials require continuous monitoring to detect when damage occurs due to the transient nature of the light flash.

Smart coatings consisting of several layers of sensing materials have also been reported.[4] These are complex and require external power to accomplish many of their tasks. A diacetylene segmented copolymer is known which exhibits a shift in color when subjected to a strain.[5]

In the chemistry literature, Todres outlines several organic compounds that have displayed mechanochromic properties.[6] Specifically, spiropyran has been noted to undergo a color change upon grinding;[7] however, little application exists for the small molecule alone.

Weder and coworkers have incorporated cyano-substituted oligo(p-phenylene vinylene) derivatives into different polymer matrixes and have synthesized "self-assessing" polyurethanes, polyethylene blends, poly(ethylene terephthalate)s, and poly(ethylene terephthalate glycol)s.[8a-e] Their approach relies on the initial formation of nanoscale aggregates of the sensor molecules in the polymer matrix. Upon deformation the cyano-substituted oligo(p-phenylene vinylene) sensors are transformed from excimer to monomer and a shift in the emission spectrum is observed. Most of these sensing units are not chemically incorporated into the backbone, and many exhibit only a fluorescent color change that is not visible to the naked eye. Additionally, these materials are not reversible and can only exhibit a color change once.

Finally, Kim and Reneker introduced an azobenzene into a copolyamide oligomer, which was chemically incorporated into a polyurethane.[9] Upon exposing the material to tensile stress, a change in the UV spectrum at 375 nm was observed. However, no visible change was noted and the polymer had to be irradiated with UV light prior to stressing the material.

SUMMARY

In a first aspect, the present invention is a mechanochromic material, comprising a polymer having a backbone containing a mechanophore.

In a second aspect, the present invention is a polymer having a backbone containing a mechanophore.

In a third aspect, the present invention is a method of making a polymer, comprising forming a polymer having a backbone containing a mechanophore.

BRIEF DESCRIPTION OF THE DRAWINGS

FIG. 5 a is for low molecular weight (18 kDa) and FIG. 5 b is for intermediate molecular weight (91 kDa). The top graph is before stress, and the bottom graph is after stress.

FIGS. 8 a, b and c illustrate the appearance of the polymer before stress (a), after stress (b) and after 2 hours exposure to light (c).

FIG. 9 is a graph of the absorbance under the same three conditions.

FIG. 10 illustrates the control before (a) and after (b) stress.

FIG. 11 illustrates the effect of the location of the mechanophore within the polymer backbone.

FIG. 12 illustrates the damage induced color change of the spiropyran containing polymer of the present invention, with a molecular weight of 170 kDa and 0.4 wt % spiropyran.

DETAILED DESCRIPTION

The present invention includes a polymer which incorporates a chemical into the polymer backbone that signals an area under stress by causing a color change in the material. This allows for damage detection via a color change of the material and thus early repair before failure, ultimately extending the lifetime of the product.

The chemical incorporated into the polymer backbone is a stress-responsive mechanophore. One mechanophore moiety is placed in the center of the polymer backbone and undergoes a structural change in response to stress. This change causes a color change of the polymer material. The color change may be a visible to the unaided eye color change.

There are several advantages to this method of stress/damage detection. The damage sensing mechanophore is chemically incorporated into the polymer backbone and hence is distributed evenly throughout the material. Since the mechanophore is chemically incorporated, no extra processing steps are required post-polymerization and the mechanophore cannot be eliminated by everyday wear. Finally, damage can be detected visually without removing parts or using expensive detection equipment such as UV or x-ray monitors.

Since our mechanophore is incorporated at the molecular level into the polymer, it is evenly dispersed throughout the matrix by default. The color change of our material is persistent over minutes to hours depending on conditions. All energy required to obtain the color change in our material is provided by the damaging force. The polymer is virtually colorless when unstressed and develops a vivid color when stressed. The appearance rather than the shift in color would be expected to be easier to detect.

The mechanophore can be incorporated into different polymers, including PMMA, PS, and PVC. Examples of mechanophores include spiropyran and moiety I.

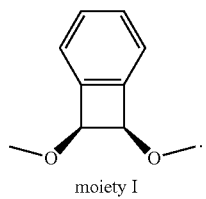

moiety I

When under stress, the force on a polymer is largest in the polymer's center. Therefore, the mechanophore is preferably positioned at or near the midpoint of the polymer backbone. The force increases with molecular weight, and therefore selective mechanochemistry may be controlled by controlling the molecular weight of the polymer. Low PDI is preferred. The threshold molecular weight for activation in a flow cell threshold is about 106 Da.

Bidirectional Living Polymerization with Difunctional Mechanophore Initiator

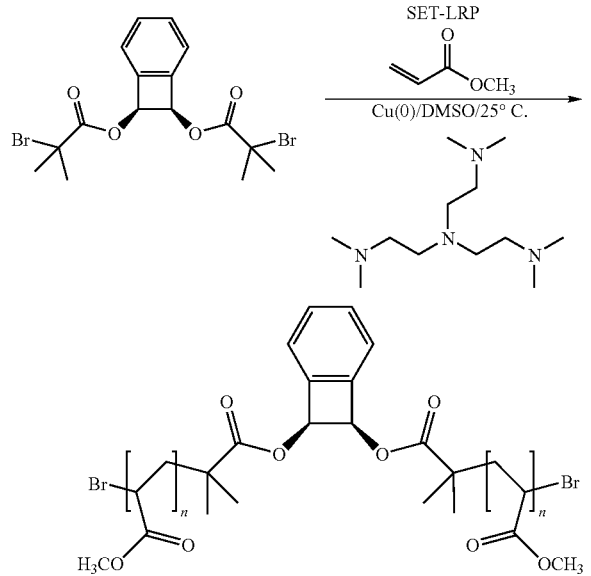

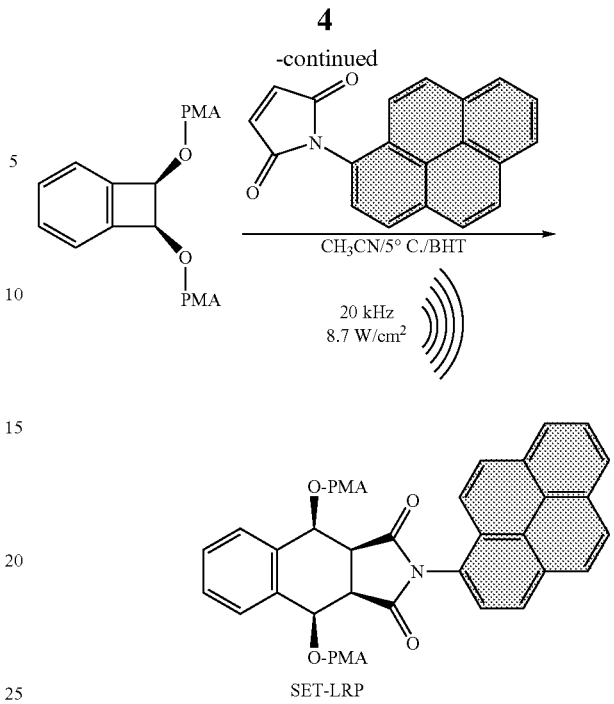

Figure 3:
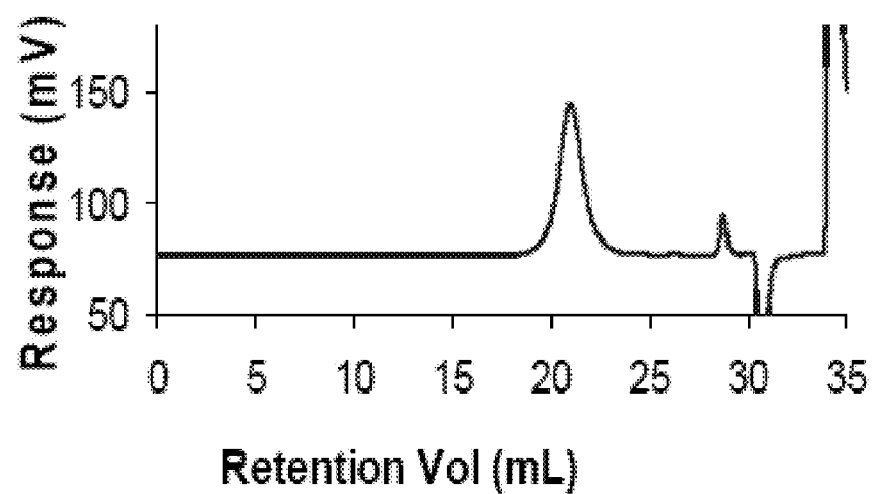
FIG. 3 shows the response in mV for retention volume in mL.
Figure 4:
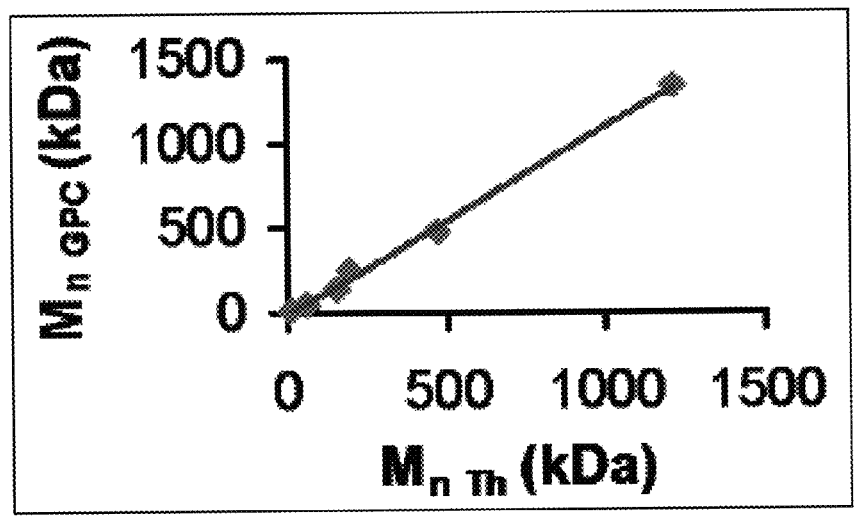
FIG. 4 shows $M_{n\ GPC}$ in kDa versus $M_{n\ Th}$ in kDa.
Figure 5:
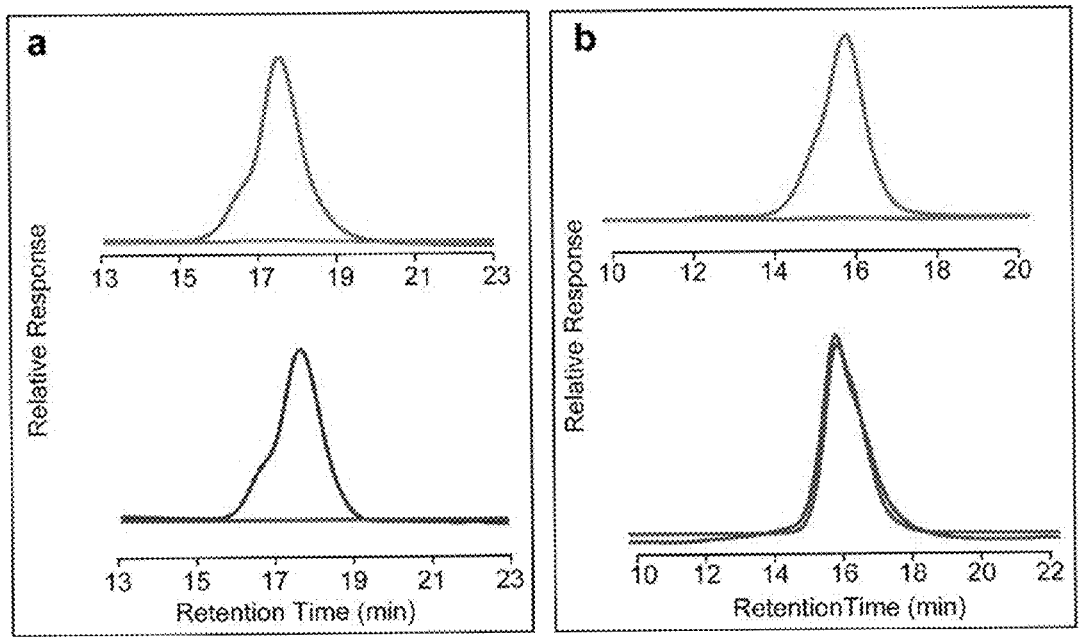
FIGS. 5 a and b show the effect of molecular weight.
Figure 6:
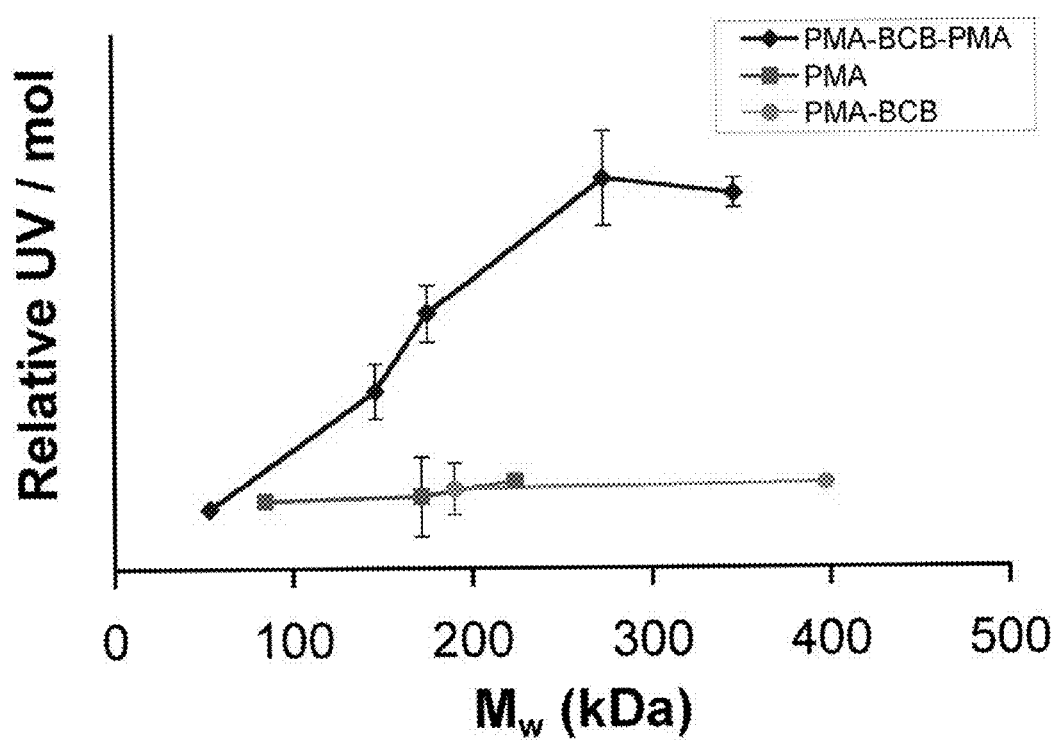
FIG. 6 shows the molecular weight dependence of mechanochemical activity.

FIG. 3 shows the response in mV for retention volume in mL. FIG. 4 shows $M_{n\ GPC}$ in kDa versus $M_{n\ Th}$ in kDa. SET-LRP is described in reference 10. The reaction scheme below shows the mechanophore reaction under stress. FIGS. 5 $a$ and $b$ show the effect of molecular weight; FIG. 5 $a$ is for low molecular weight (18 kDa) and FIG. 5 $b$ is for intermediate molecular weight (91 kDa). The top graph is before stress, and the bottom graph is after stress. FIG. 6 shows the molecular weight dependence of mechanochemical activity.

Color-Generating Mechanophore

When incorporated into a polymethacrylate (PMA) backbone, the polymer changes color upon stretching and tearing. We analyzed the results in solution and solid state to prove that the color change is a result of the mechanochemical (stress-induced) reaction of spiropyran.

Figure 1A:
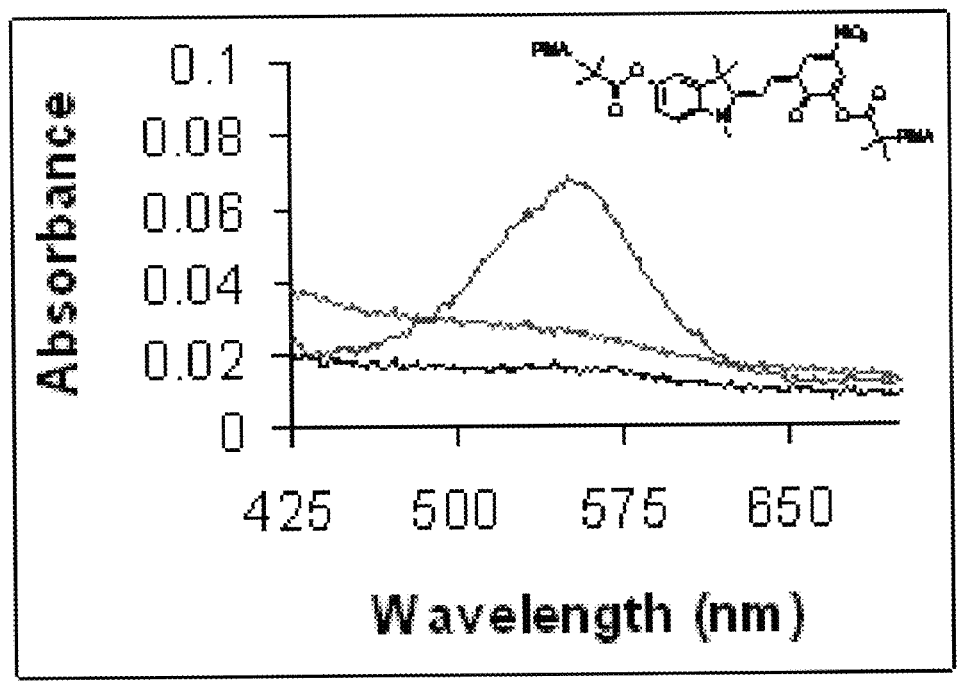
FIG. 1. a. UV spectrum of PMA-SP-PMA before (darkest line) and after (lightest line) sonication. The polymer returns to its original color after sitting in ambient light (intermediate line). b. UV spectrum of end functionalized PMA-SP mechanically-inactive control before (darkest line) and after (lightest line) sonication.
Figure 1B:
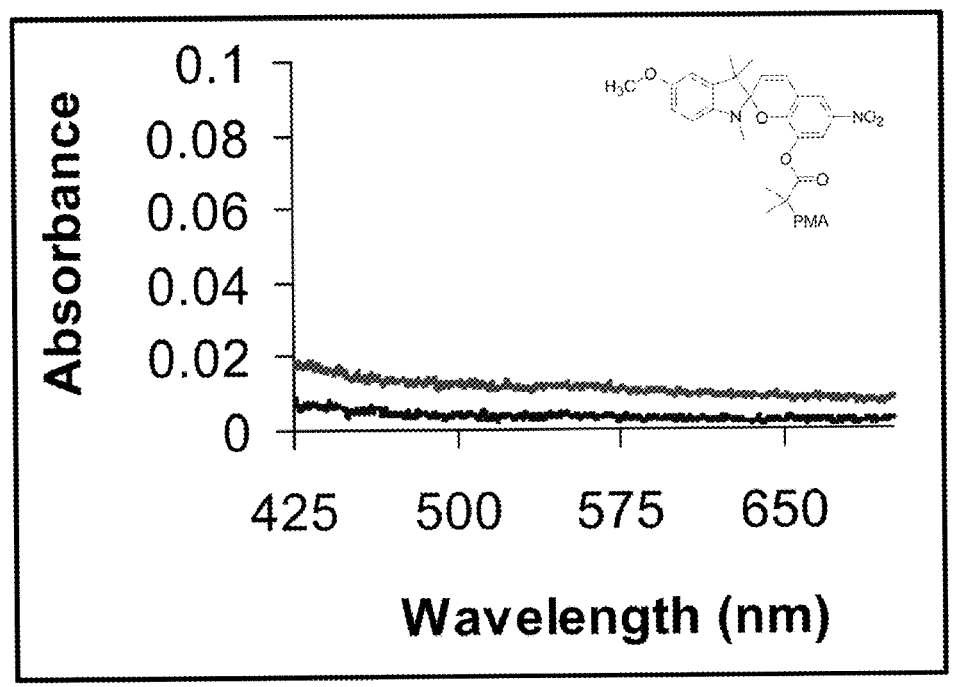

Ultrasound has been used to elongate and stress polymers in solution and study the mechanochemical reactivity of compounds. The PMA polymer containing the spiropyran near the center of the polymer backbone (where mechanical forces are the greatest) was stressed using ultrasound and analyzed using a ultraviolet (UV) spectrophotometer. The results are illustrated in FIG. 1. The increase in the UV absorbance of the sonicated (mechanically stressed) spiropyran polymer corresponds to the colored form of the spiropyran. A mechanically inactive spiropyran polymer (spiropyran is located at the end of the polymer chain where ultrasound does not mechanically stress the polymer) was tested and no change in the UV signal occurred. These experiments show that the color change is due to the mechanically induced structural change in the spiropyran.

Figure 2:
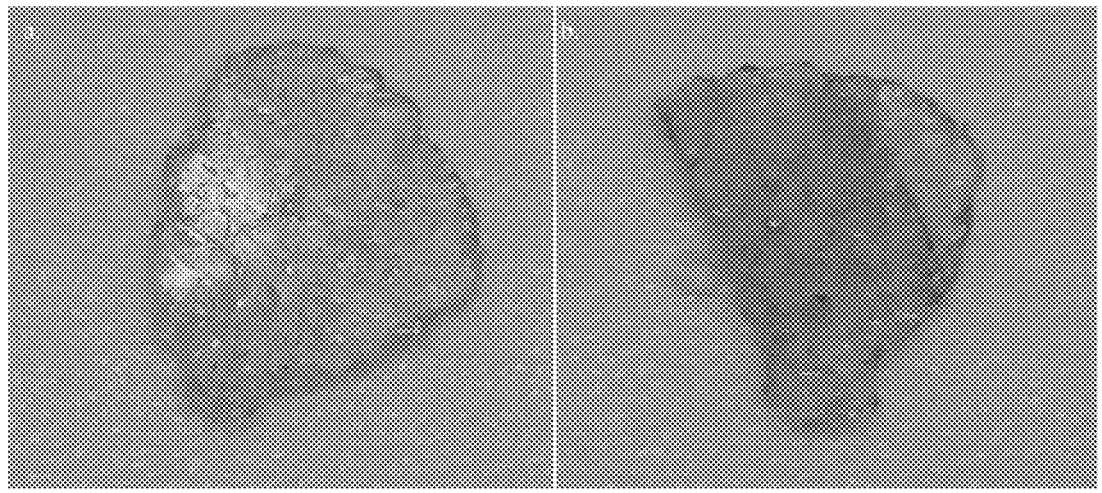
FIG. 2. a. PMA-SP-PMA before mechanical stress has been applied. b. PMA-SP-PMA after mechanical stress has been applied, showing a pink color in the areas of highest stress.

Studies were also carried out in the solid state. Upon stretching and tearing the spiropyran polymer, a color change was observed. The originally yellowish polymer changed to a pink color where it was under stress (FIG. 2).

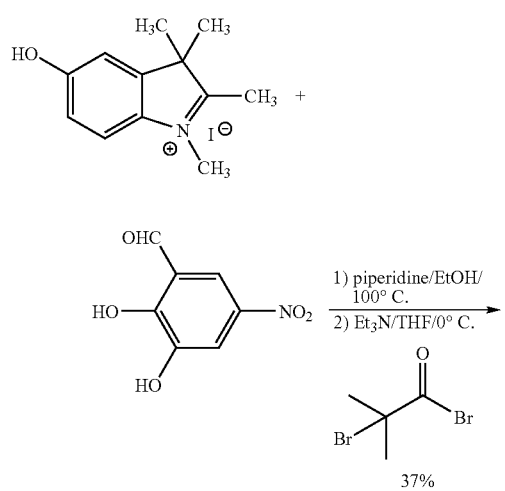

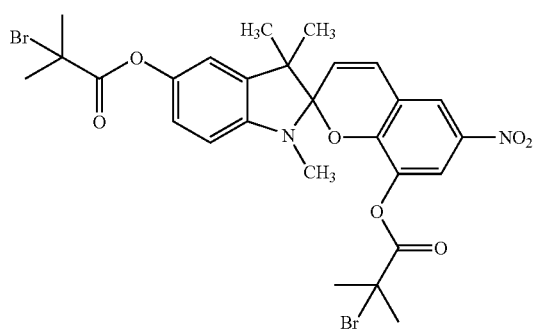

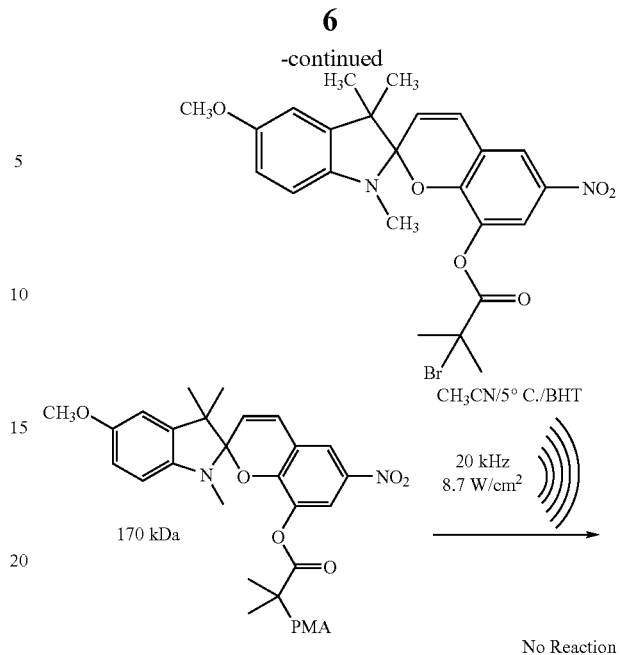

Figure 7:
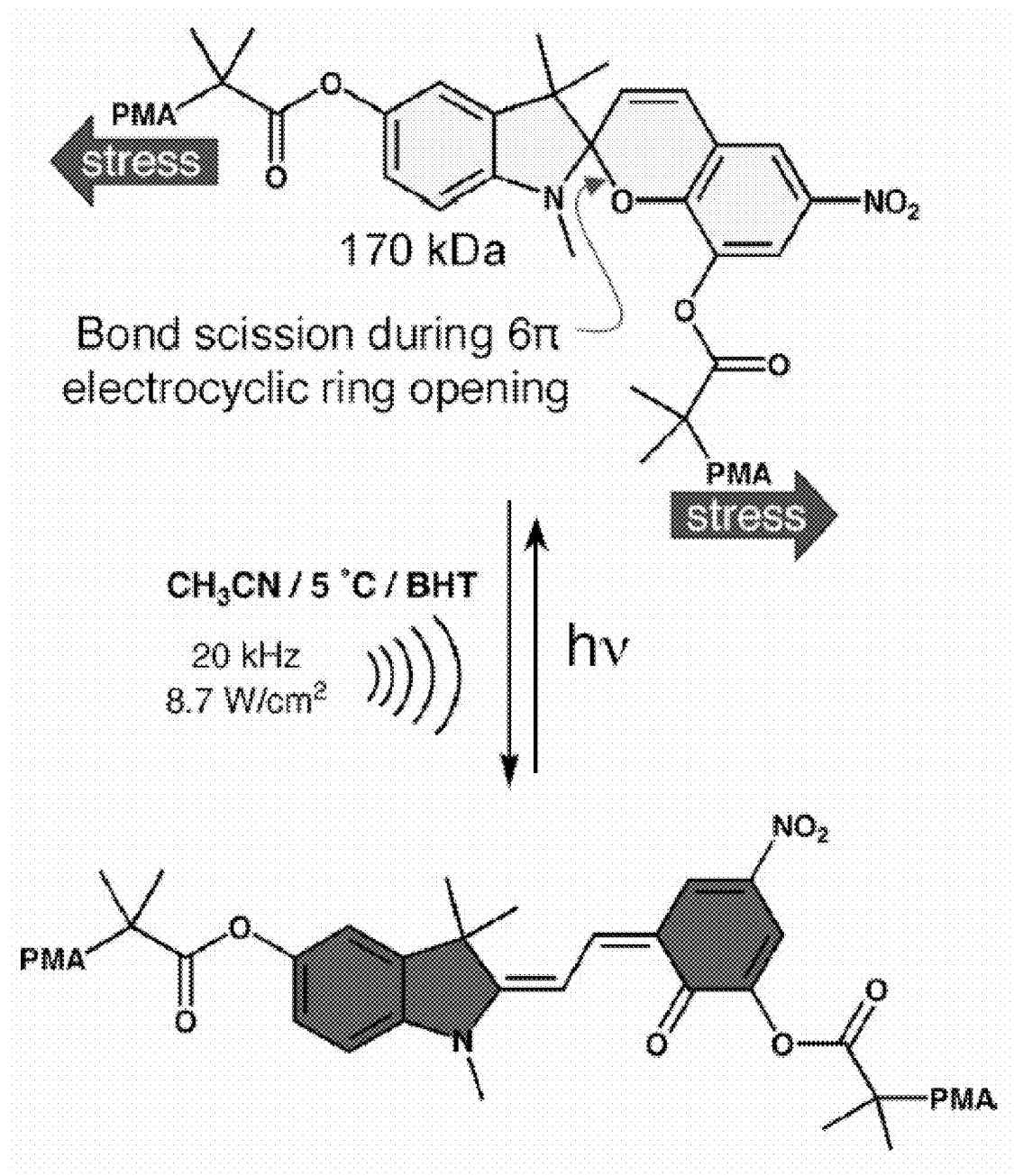
FIG. 7 illustrates the chemical reaction of spiropyran under stress, and when subsequently exposed to light.

FIG. 7 illustrates the chemical reaction of spiropyran under stress, and when subsequently exposed to light. FIGS. 8 a, b and c illustrate the appearance of the polymer before stress (a), after stress (b) and after 2 hours exposure to light (c). FIG. 9 is a graph of the absorbance under the same three conditions.

The following monofunctional initiator was prepared as a control.

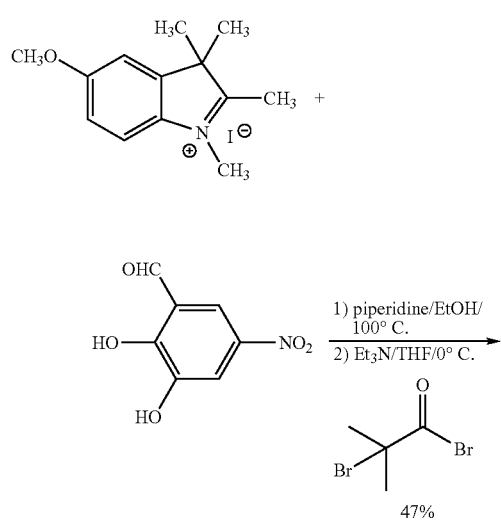

FIG. 10 illustrates the control before (a) and after (b) stress. There is no change in color. FIG. 11 illustrates the effect of the location of the mechanophore within the polymer backbone. FIG. 12 illustrate the damage induced color change of the spiropyran containing polymer of the present invention, with a molecular weight of 170 kDa and 0.4 wt % spiropyran.

REFERENCES

1. Koene, B. E.; Rogers, M. E. WO patent 2006105290, 2006.
2. Dunleavy, M.; Haq, S. WO patent 2007003883, 2007.
3. Sage, I. C.; Howie, W. H.; Brotherston, I. D. U.S. Pat. No. 7,242,443, 2007.
4. Watts, D. J.; Battista, L.; Zunino, J.; Colon, N.; Federici, J.; Thomas, G.; Lim, H. C.; Iqbal, Z.; Argento, J.; Grebel, H.; Mitra, S.; Zhang, Y. U.S. Pat. No. 7,244,500, 2006.
5. Rubner, M. F. U.S. Pat. No. 4,721,769, 1986.
6. Todres, Z, V. J. Chem Res. 2004, 89-93.
7. Tipikin, D. S., Zh. Fiz. Khim., 2001, 75, 1876.
8. (a) Crenshaw, B. R., Weder, C. Macromolecules 2006, 39, 9581-9589.
    (b) Crenshaw, B. R., Burnworth, M., Khariwala, D., Hiltner, A., Mather, P. T., Simha, R., Weder, C. Macromolecules 2007, 40, 2400-2408.
    (c) Lowe, C. Weder, C. Adv. Mater. 2002, 12(22), 1625.
    (d) Crenshaw, B. R., Weder, C. Chem. Mater. 2003, 15, 4717.
    (e) Kinami, M., Crenshaw, B. R., Weder, C. Chem. Mater. 2006, 18, 946.
9. Kim, S., Reneker, D. H., Polym Bull. 1993, 31, 367-374.
10. Percec et al. JACS 2006.

What is claimed is:

1. A mechanochromic material, comprising a polymer having a backbone containing a mechanophore;
    the mechanophore selected from the group consisting of a spiropyran and moiety I having the structure:

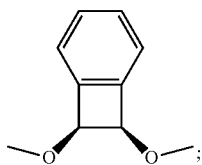

where, upon the application of stress, the mechanophore undergoes a chemical reaction, and the mechanochromic material undergoes a visible change in color.

2. The mechanochromic material of claim 1, wherein the polymer is selected from the group consisting of a polymethacrylate, a polymethylmethacrylate, a polystyrene, and a polyvinyl chloride.

3. A polymer having a backbone containing a mechanophore;
the mechanophore selected from the group consisting of a spiropyran and moiety I having the structure:

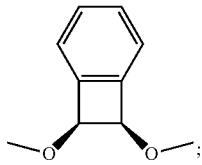

where, upon the application of stress, the mechanophore undergoes a chemical reaction, and the polymer undergoes a visible change in color.

4. The polymer of claim 3, wherein the polymer is selected from the group consisting of a polymethacrylate, a polymethylmethacrylate, a polystyrene, and a polyvinyl chloride.

5. A method of making the polymer of claim 3, comprising forming a polymer having a backbone containing a mechanophore.

6. The method of claim 5, wherein the polymer is selected from the group consisting of a polymethacrylate, a polymethylmethacrylate, a polystyrene, and a polyvinyl chloride.

7. A method of monitoring stress on a structure, comprising:
forming the structure from the mechanochromic material of claim 1
using the structure; and
examining the mechanochromic material for a visible color change.

8. The method of claim 7, wherein the polymer is selected from the group consisting of a polymethacrylate, a polymethylmethacrylate, a polystyrene, and a polyvinyl chloride.

9. The mechanochromic material of claim 1,
where the polymer comprises polymethacrylate.

10. The polymer of claim 6,
where the polymer comprises polymethacrylate.

11. The method of claim 5,
where the polymer comprises polymethacrylate.

* * * * *

UNITED STATES PATENT AND TRADEMARK OFFICE
CERTIFICATE OF CORRECTION

| | | |
|---|---|---|
| PATENT NO. | : 8,236,914 B2 | Page 1 of 1 |
| APPLICATION NO. | : 12/693801 | |
| DATED | : August 7, 2012 | |
| INVENTOR(S) | : Potisek et al. | |

It is certified that error appears in the above-identified patent and that said Letters Patent is hereby corrected as shown below:

In the Specification

Column 1, Line 12 please add the following sentence to the first paragraph:

[001] This application is a continuation of PCT/US2008/071083 entitled "Self-Assessing Mechanochromic Materials" filed July 24, 2008, which was published in English and claimed the benefit of U.S. Provisional Application No. 60/952,550 entitled "Self-Assessing Mechanochromic Materials" filed July 27, 2007, which are incorporated by reference in their entirety. This Invention was made with government support under award number W911NF-07-1-0409 from the United States Army. The government has certain rights in the invention.

Signed and Sealed this
Fifteenth Day of April, 2014

Michelle K. Lee
*Deputy Director of the United States Patent and Trademark Office*